United States Patent [19]

Ferres

[11] 4,150,157

[45] Apr. 17, 1979

[54] PENICILLIN COMPOSITIONS

[75] Inventor: Harry Ferres, Horsham, England

[73] Assignee: Beecham Group Limited, United Kingdom

[21] Appl. No.: 833,871

[22] Filed: Sep. 16, 1977

Related U.S. Application Data

[62] Division of Ser. No. 800,281, May 25, 1977.

[30] Foreign Application Priority Data

Jun. 11, 1976 [GB] United Kingdom ............... 24219/76

[51] Int. Cl.² .......................................... A61K 31/535

[52] U.S. Cl. ............................. 424/248.51; 260/239.1

[58] Field of Search ................. 424/248.51; 260/239.1

[56] References Cited

FOREIGN PATENT DOCUMENTS 2531144 1/1976 Fed. Rep. of Germany ........... 424/271

Primary Examiner—Jerome D. Goldberg
Attorney, Agent, or Firm—Jacobs & Jacobs

[57] ABSTRACT

A class of substituted aminoalkyl esters of methicillin have good oral absorption properties.

8 Claims, No Drawings

PENICILLIN COMPOSITIONS

CROSS REFERENCE

This is a division of Ser. No. 800,281 filed May 25, 1977.

This invention relates to pharmaceutical compositions comprising penicillin esters which upon oral administration are absorbed into the bloodstream where they are hydrolysed to release the antibacterially active parent penicillin.

In particular it is concerned with compositions containing substituted aminoalkyl esters of the penicillin, methicillin, which has the formula (I):

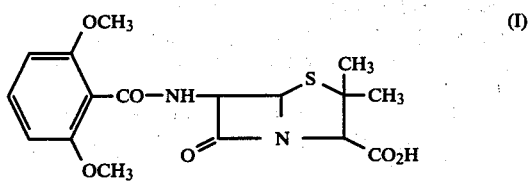

The diethylaminoethyl ester of benzylpenicillin is a known compound, used for the treatment of bovine mastitis. Although better "tissue penetration" properties are achieved with this ester compared with benzylpenicillin itself, the ester is not absorbed by the oral route to any appreciable extent.

British Patent Specification No. 1,470,154 discloses a class of penicillin dialkylaminoalkyl esters of the formula (II):

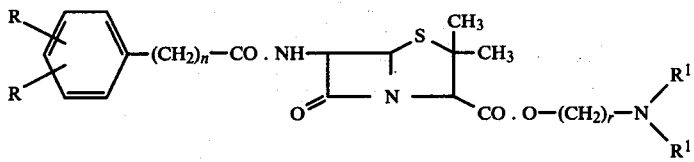

(wherein R is hydrogen, $C_{1-4}$ alkyl, hydroxy, methoxy or ethoxy, $R^1$ is alkyl, n is 0 or 1 and r is 1–10) for the treatment of mastitis. Although dialkylaminoalkyl esters of methicillin are disclosed, specifically the diethylaminoethyl ester, there is no suggestion that any of these esters are effective when administered orally.

It has now been found that a class of substituted aminoalkyl esters of methicillin have good oral absorption characteristics.

Accordingly the present invention provides a pharmaceutical composition comprising a pharmaceutically acceptable carrier together with a methicillin ester of formula (III):

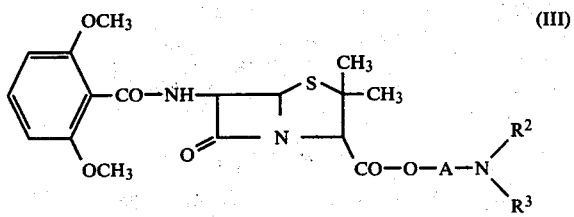

or a pharmaceutically acceptable acid-addition salt thereof, wherein A is a $C_1$-$C_6$ alkylene group optionally substituted by one or more methyl or ethyl groups, and $R^2$ and $R^3$ are the same or different and each is a $C_1$-$C_6$ alkyl group, or $R^2$ and $R^3$ together with the nitrogen atom to which they are attached form a saturated 5- or 6-membered heterocyclic ring, the composition being adapted for oral administration to humans. Suitable acid addition salts of the compounds of formula (III) include, for example inorganic salts such as the sulphate, nitrate, phosphate, and borate; hydrohalides e.g. hydrochloride, hydrobromide and hydroiodide; and organic acid addition salts such as acetate, oxalate, tartrate, maleate, citrate, succinate, benzoate, ascorbate, methanesulphonate, and p-toluenesulphonate, trifluoroacetate.

A preferred acid addition salt is the hydroiodide.

A preferred group A is an ethylene group of formula $-CH_2-CH_2-$.

Suitable examples of alkyl groups for $R^2$ and $R^3$ include methyl, ethyl, n- and iso-propyl and n-, iso-, sec- and tert-butyl. Preferably $R^2$ and $R^3$ are the same and are both methyl or ethyl groups. When $R^2$ and $R^3$ complete a heterocyclic ring, they preferably comprise an alkylene chain optionally interrupted with an oxygen or nitrogen atom. Suitable rings include the following:

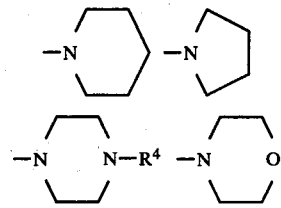

(wherein $R^4$ is hydrogen or alkyl) Suitable compounds for inclusion into the present compositions include the 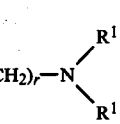 following methicillin esters:

diethylaminoethyl;
dimethylaminoethyl;
2-N-morpholinoethyl.

The fact that the small class of methicillin esters of formula (III) are well absorbed orally is not predictable from the prior art referred to above where there is no suggestion of oral use. Furthermore, corresponding esters of similar penicillins do not possess oral absorption characteristics. Thus Tables 1 and 2 at the end of this specification demonstrate that whereas the diethylaminoethyl ester of methicillin produces high levels of the parent penicillin in blood after oral administration to mice and squirrel monkeys, for the same esters of the closely related benzylpenicillin and cloxacillin, the absorption was inferior to that of the parent penicillins.

The compositions of this invention are adapted for oral administration to humans. They may be in the form of tablets, capsules, powders, granules, lozenges, syrups or elixirs.

Tablets and capsules for oral administration may be in unit dose presentation form, and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily syrups, or elixirs. Such liquid preparations may contain conventional additives such as suspending agents, for example sorbitol, syrup, methylcellulose, glycose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The compositions may contain from 0.1% to 99% by weight, preferably from 10-60% by weight, of the active material, depending on the method of administration. Where the compositions comprise dosage units, each unit will preferably contain from 50-500 mg., of the active ingredient. The dosage as employed for adult human treatment will preferably range from 100 to 3000 mg., per day, for instance 1500 mg., per day, depending on the route and frequency of administration.

The ester of formula (III) may be present in the composition as sole therapeutic agent or it may be present with other therapeutic agents. Advantageously a synergistic combination may be produced by incorporating a β-lactam inhibitor of formula (IV) or a pharmaceutically acceptable salt or ester thereof into the composition:

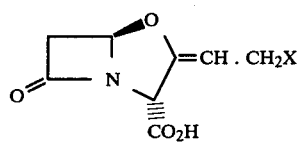   (IV)

wherein X is hydrogen or hydroxyl.

Preferably the compound of formula (IV) is clavulanic acid of formula (I):

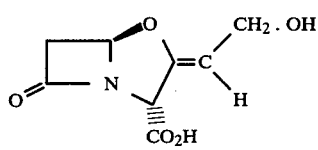   (V)

The preparation of compounds of formula (IV) is described in Belgian Pat. Nos. 827,926 and 836,652 and West German Offenlegungsschrift No. 2,616,088.

The esters of formula III are in general known compounds and may be prepared by conventional methods. Preferably methicillin of formula (I) above or a reactive esterifying derivative thereof is reacted with a compound of formula (VI) or a reactive esterifying derivative thereof:

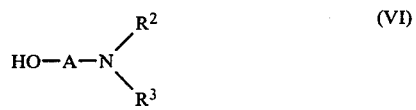   (VI)

wherein A, $R^2$ and $R^3$ are as defined with respect to formula (III).

By the term "reactive esterifying derivative" in relation to compounds (I) and (VI) above, we mean derivatives of (I) and (VI) which when reacted together take part in a condensation reaction with the consequent formation of an ester linkage:

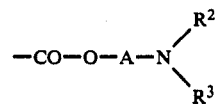

Many methods of esterification using several different combinations of reactive esterifying derivatives are known from the literature. For example, the esterification reaction defined above may be achieved by reacting an activated ester of methicillin with an alcohol of formula VI. Preferred activated ester groups are mixed anhydrides, but other activated ester groups include the acid halide, e.g. acid chloride, and the reactive intermediate formed with a carbodiimide or carbonyldiimidazole.

Alternatively methicillin or a salt thereof, preferably the sodium or potassium salt, may be reacted with a halide, alkylsulphonyl (e.g. methansulphonyl) or arylsulphonyl (e.g. p-toluenesulphonyl) ester of compound (VI).

The compounds of formula (III) may also be prepared by N-acylation of the corresponding esterified 6-aminopenam; that is by reacting a compound of formula (VII):

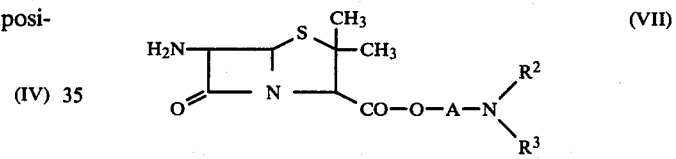   (VII)

or an N-protected derivative thereof, wherein A, $R^2$ and $R^3$ are as defined with respect to formula (III), with a reactive N-acylating derivative of the compound of formula (VIII):

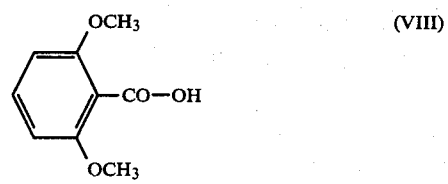   (VIII)

As the substituted amino ester grouping in formula (III) is labile to chemical hydrolysis, the above reaction should be carried out in anhydrous media.

In the following specific Examples, Example 1-3 illustrate the preparation of some esters of formula (III) and Example 4 illustrates compositions according to this invention:

EXAMPLE 1

2-N,N-Diethylaminoethyl 2,6-dimethoxybenzamido penicillanate, hydroiodide

Sodium 2,6-dimethoxybenzamido penicillanate (monohydrate) (4.20 g; 0.01 M) was suspended in dry methylene dichloride (75 ml.) between −10° and −15° C. with stirring while isobutylchloroformate (1.36 g; 0.01 M) was added in one portion plus 2-3 drops of pyridine. After ½ hour reaction with continuous stirring and maintaining the temperature of −10° C. the solution containing the penicillin isobutoxyformic anhydride was cooled to −12° and filtered to remove the precipitated sodium chloride. The clear pale yellow filtrate was stirred at −10° C. while a solution of diethylaminoethanol (1.17 g; 0.01 M) in methylene dichloride (25 ml.) was added in one portion. The reaction mixture was stirred for 2 to 2½ hours without any further external cooling. After evaporation of the solvent the residual oil was dissolved in ethyl acetate (100 ml.) and washed with water (2×100 ml.). The solution was dried over anhydrous magnesium sulphate and evaporated to an oil. The hydroiodide salt of the penicillin ester was prepared by forming a solution of the free base oil in acetic acid (ca 2 ml.) and water (10–15 ml.) at 0° C. and adding a solution of sodium iodide (2.0 g) in water (1 ml.). After stirring at 0° C. for 15 mins., the precipitated gum was washed with water and dissolved in methylene dichloride (20 ml.), dried over anhydrous magnesium sulphate, concentrated to about one fifth its volume and added slowly and carefully to diethyl ether at 0° C. with stirring. The product was precipitated as a white, amorphous hydroiodide salt, 1.62 g (27% yield).

m.p. 99° C. (dec) (Found: C, 46.2; H, 5.8; N, 6.6; S, 5.4%. $C_{23}H_{34}IN_3O_6S$ requires C, 45.5; H, 5.6; N, 6.9; S, 5.3%). γ max (KBr) 3400 (br.), 1778, 1748, 1667, 1594, 1473, 1255 and 1108 $cm^{-1}$. $\delta[(CD_3)_2SO]$ 1.20 (t) and (3.12 (q) ($CH_3CH_2$), 1.46(s) and 1.62(s) (gemdimethyls), 3.45(m) and 4.36(m) ($CH_2CH_2O$), 3.71(s) (2×$OCH_3$). 5.5–5.9(m) (β-lactams), 6.62 (d) and 7.28(m) ($C_6H_3$), 8.87 (d) (CONH), biochromatogram (B/E/W) Rf 0.68.

EXAMPLE 2

2-N,N-Dimethylaminoethyl 2,6-dimethoxybenzamido penicillanate, hydroiodide.

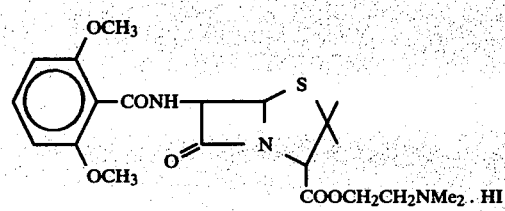

This compound was synthesised using the method as for Example 1 except that a mixed anhydride of methicillin formed by reaction with tert-butyl carbonyl chloride rather than iso-butylchloroformate was used.

Reaction scale: 0.005 M.

Yield of product: 45%

γ max (KBr) 3400(br), 1780, 1750, 1660, 1595, 1475, 1300, 1255 and 1100 $cm^{-1}$ $\delta[(CD_3)_2SO]$: 1.46(s) and 1.63(s) (gem-dimethyls), 2.66(s) (—N($CH_3$)$_2$), 3.73(s) (2×O$CH_3$), 4.38(br) (—$CH_2$OCO—), 4.40(s) ($C_3$-proton), 5.75(m) (β-lactam protons), 6.68(d) and 7.32(m) (aromatic protons), 8.8(d) (CONH*), *exchangeable with $D_2O$, biochromatogram (B/E/W) Rf 0.65 (single zone).

EXAMPLE 3

2-N-Morpholinoethyl 2,6-dimethoxybenzamido penicillanate, hydroiodide

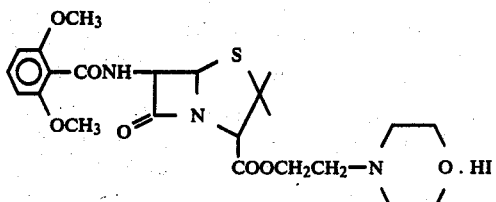

This compound was synthesised using the method described for Example 1.

Reaction scale: 0.005 M

Yield of product: 16%

γ max (KBr): 3450(br), 1780, 1750, 1665, 1595, 1475, 1255 and 1105 $cm^{-1}$ $\delta[(CD_3)_2SO]$: 1.50(s) and 1.64(s) (gem-dimethyls), 3.2(m)

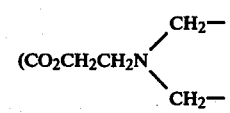

3.75(s) (2×O$CH_3$), 3.8(m)

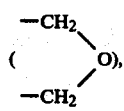

4.42(s) (C-proton), 4.5(m)($CO_2CH_2CH_2N<$), 5.75(m) (β-lactam protons), 6.68(d) and 7.35(m) (aromatic protons), 8.88(d) (CONH*). *exchangeable with $D_2O$, biochromatogram (B/E/W) Rf 0.88 (single zone).

EXAMPLE 4

The following compositions are prepared as oral formulations containing the compound of Example 1, designated compound 1:

| (a) Capsule | per capsule |
|---|---|
| Compound 1, equivalent to methicillin, | 250mg. |
| Magnesium stearate (lubricant) | 5mg. |

| (b) Syrup: | per 5ml dose | per 100ml bottle |
|---|---|---|
| Compound 1, equivalent to methicillin | 250mg. | 5.0mg. |
| Sodium benzoate (preservative) | 5mg. | 0.1g. |
| Flavours | q.s.* | q.s. |
| Colouring | q.s. | q.s. |
| Sucrose to | 3.35g. | 67g. |

*q.s. = sufficient quantity

The powdered product is reconstituted at the time of dispensing by adding 60 ml., of water per 100 ml. bottle, and shaking until homogeneous.

| (c) | Tablets: | per tablet |
|---|---|---|
| | Compound 1, equivalent to methicillin | 250mg. |
| | Magnesium stearate (lubricant) | 5mg. |
| | 'Primogel' (disintegrant) | 7mg. |
| | 'Avicel' (dried) (bulking agent) to | 360mg. |

Compositions (a), (b) and (c) are also prepared in a similar manner for the compounds of Examples 2 and 3.

Biological Data

Experiment 1

In Vivo Absorption Data: Squirrel Monkey Blood Levels after oral (P.O.) dosing at 100 mg/kg penicillin free acid equivalent (Cross-over Studies)

Table 1 below shows a comparison of the absorption characteristics of the diethylaminoethyl esters of penicillin G+, cloxacillin* and methicillin+ with the parent penicillins (sodium salts).
*hydrochloride salt +hydroiodide salts Table 1

| Compound | Mean Concentrations of Parent Penicillin in μg/ml at hrs after dosing | | | | | |
|---|---|---|---|---|---|---|
| | 0.25 | 0.5 | 1.0 | 2.0 | 4.0 | 6.0 |
| Penicillin G Ester | 2.2 | 2.1 | 1.31 | 0.36 | 0.077 | 0.022 |
| Acid | 8.5 | 7.8 | 4.9 | 0.50 | 0.24 | 0.10 |
| Cloxacillin Ester | <0.4 | 1.2 | 1.7 | 0.52 | <0.4 | <0.4 |
| Acid | 9.4 | 15.4 | 5.32 | 1.85 | <0.5 | <0.5 |
| Methicillin Ester | 14.1 | 14.0 | 11.4 | 6.1 | 2.0 | 0.43 |
| Acid | 1.6 | 2.3 | 1.4 | 0.67 | 0.15 | <0.10 |

*hydrochloride
+hydroiodide salts

Table 1 shows that whereas the diethyl aminoethyl esters of penicillin G and cloxacillin are considerably less well absorbed than the free acid itself in squirrel monkeys, the corresponding ester of methicillin is markedly better absorbed than methicillin itself.

Experiment 2

In Vivo Absorption Data: Mouse Blood Levels after Oral Dosing at 50 mg/kg (a) Comparison of the absorption properties of the diethylaminoethyl esters (hydroiodide salts) of penicillin G, cloxacillin and methicillin with the parent penicillins (sodium salts).

Table 2

| Compound | Mean Concentrations of Parent Penicillin in μg/ml at Mins after dosing | | | | |
|---|---|---|---|---|---|
| | 10 | 20 | 30 | 60 | 120 |
| Penicillin G Ester | 1.93 | 1.08 | 0.52 | 0.18 | 0.019 |
| Acid | 1.13 | 1.07 | 0.56 | 0.22 | 0.08 |
| Cloxacillin Ester | 0.57 | 1.1 | 0.46 | 0.19 | <0.1 |
| Acid | 2.08 | 5.01 | 3.3 | 2.25 | 0.43 |
| Methicillin Ester | 5.35 | 4.4 | 2.4 | 0.6 | <0.1 |
| Acid | 0.036 | 0.035 | 0.067 | 0.11 | <0.05 |

Table 2 shows a marked improvement, in the oral absorption of the diethylaminoethyl ester of methicillin in mice compared with methicillin itself; whereas the corresponding ester of penicillin G shows no significant improvement over penicillin G itself and the corresponding ester of cloxacillin is considerably less well absorbed than cloxacillin.

(b) Table 3 shows the mouse blood levels for each of the compounds of Examples 1–3.

TABLE 3

| | Mouse blood levels after oral dosing at 50mg/Kg | | | | |
|---|---|---|---|---|---|
| Example Number | Mean Concentrations of methicillin in μg/ml at mins after ORAL dosing | | | | |
| | 10 | 20 | 30 | 60 | 120 |
| 1 | 5.35 | 4.4 | 2.4 | 0.6 | <0.1 |
| 2 | 3.84 | 4.6 | 0.75 | 0.25 | <0.1 |
| 3 | 5.9 | 6.7 | 2.1 | 0.51 | <0.1 |
| METHICILLIN SODIUM SALT | 0.036 | 0.035 | 0.067 | 0.11 | <0.1 |

EXPERIMENT 3: IN VITRO DATA

Rates of in vitro hydrolysis of methicillin alkylaminoalkyl esters to methicillin in blood and buffered saline (pH 7.4)

TABLE 4

| Example Number | Hydrolysis System | Percentage Hydrolysis To Methicillin At Various Times (in mins) | | | |
|---|---|---|---|---|---|
| | | 15 | 30 | 45 | 60 |
| 1 | 90% Human Blood | 58 | 64 | — | 75 |
| | 9% Human small intestine | 43 | 94 | 100 | 100 |
| | 0.9% Human liver | 45 | 70 | 95 | 100 |
| | 90% Mouse blood | 100 | 100 | 100 | 100 |
| | 9% Mouse blood | 96 | 100 | 100 | 94 |
| | 0.9% Mouse blood | 50 | 63 | not | assayed |
| | 90% Squirrel Monkey | 25 | 32 | 46 | 47 |
| | Buffered Saline, pH 7.4 | 68 | 100 | 100 | 100 |
| 2 | 90% Human Blood | 59 | 84 | 94 | 100 |
| | Buffered Saline, pH 7.4 | 68 | 88 | 98 | 100 |
| 3 | 90% Human Blood | 23 | 50 | 63 | 65 |
| | Buffered Saline, pH 7.4 | 24 | 64 | 72 | 90 |

What I claim is:

1. An antibacterial pharmaceutical composition comprising a pharmaceutically acceptable carrier together with an antibacterially effective amount of a methicillin ester of formula (III):

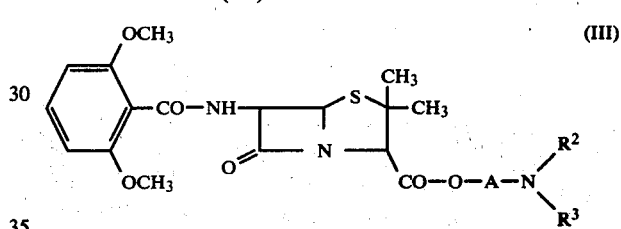

or a pharmaceutically acceptable acid addition salt thereof, wherein A is a $C_{1-6}$ alkylene group unsubstituted or substituted by methyl or ethyl, and $R^2$ and $R^3$ together with the nitrogen atom to which they are attached form the saturated 6-membered heterocyclic ring,

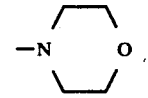

the composition being formulated for oral administration to humans.

2. An antibacterial composition as claimed in claim 1 wherein the compound of formula (III) is methicillin morpholinoethyl ester or its hydroiodide salt.

3. An antibacterial composition as claimed in claim 2 wherein the compound of formula (III) is in the form of its hydroiodide salt.

4. An antibacterial composition as claimed in claim 1 wherein the group A is ethylene.

5. An antibacterial composition as claimed in claim 1 wherein the methicillin ester is present in an amount of 0.1% to 99% by weight of the composition.

6. A method of treating bacterial infections in humans which method comprises the oral administration to a human in need thereof of an antibacterially effective amount of a composition of claim 5.

7. An antibacterial composition as claimed in claim 2 wherein the methicillin ester is present in an amount of 0.1% to 99% by weight of the composition.

8. A method of treating bacterial infections in humans which method comprises the oral administration to a human in need thereof of an antibacterially effective amount of a composition of claim 7.

* * * * *